US012570950B2

(12) United States Patent　　　　(10) Patent No.: US 12,570,950 B2
　　Whittaker　　　　　　　　　　　　(45) Date of Patent: Mar. 10, 2026

(54) MATERIALS AND METHODS FOR ALGAL INOCULATION TO EFFECT DIRECT CAPTURE OF CARBON DIOXIDE FROM AIR

(71) Applicant: John Whittaker, Caernarfon (GB)

(72) Inventor: John Whittaker, Caernarfon (GB)

( * ) Notice: Subject to any disclaimer, the term of this patent is extended or adjusted under 35 U.S.C. 154(b) by 184 days.

(21) Appl. No.: 18/376,827

(22) Filed: Oct. 4, 2023

(65) Prior Publication Data

US 2024/0110148 A1　　Apr. 4, 2024

Related U.S. Application Data

(60) Provisional application No. 63/413,031, filed on Oct. 4, 2022.

(51) Int. Cl.
　　*C12N 1/12*　　　　(2006.01)
　　*B01D 53/84*　　　(2006.01)
(52) U.S. Cl.
　　CPC ............... *C12N 1/12* (2013.01); *B01D 53/84* (2013.01); *B01D 2251/95* (2013.01); *B01D 2257/504* (2013.01)
(58) Field of Classification Search
　　CPC ....................................................... C12N 1/12
　　See application file for complete search history.

(56) References Cited

PUBLICATIONS

English machine translation of Wang et al., CN 107893031 A, 2018.*

* cited by examiner

*Primary Examiner* — Rosanne Kosson

(57) ABSTRACT

The present invention comprises a method for synthesizing a culture of psychrophilic (cold-adapted) algae, enhanced with growth-optimized accelerators into a product for deployment in extreme cold environments. This solution integrates industrial-scale microalgal cultivation with a novel form of microalgal "afforestation" targeted at uninhabited cold geozones. The system functions as a nature-based, low-cost, and scalable carbon sequestration "vaccine," designed to remove atmospheric carbon dioxide at gigaton scales.

The method aims to restore global $CO_2$ levels to pre-industrial concentrations within a decade through repeated deployments. Carbon captured through this process is intended to be sequestered over centuries with minimal or no adverse environmental impacts.

This invention represents a significant advancement in Nature-based Climate Solutions (NbCS), offering a feasible pathway toward climate change reversal rather than mere mitigation.

6 Claims, No Drawings

MATERIALS AND METHODS FOR ALGAL INOCULATION TO EFFECT DIRECT CAPTURE OF CARBON DIOXIDE FROM AIR

INTRODUCTION

The present invention relates to climate change and provides mitigation methods with capacities to capture gigatons of carbon dioxide ($CO_2$) through its efficient, low tech and low-cost deployment. Widespread deployment not only has the potential to create a carbon neutral environment at manufacture sites and through widespread deployment could eventually reverse climate change to pre-industrial levels potentially within a decade. This invention is carbon negative in both production and deployment. i.e., it entirely offsets energy costs of production, transportation, and deployment. The product itself does not produce any net $CO_2$ emissions and its whole purpose is to capture $CO_2$ from the atmosphere.

The products and methods of this invention fix carbon (as present in $CO_2$) from the atmosphere directly in situ utilizing low cost technologies and low cost energy conversion from ambient light energy to carbon sequestering chemical energy. By administering the invention product formed as a Climate Vaccine, extreme weather events associated with industrial heat absorbing gases can be reduced. The invention features incorporating selectively cultured psychrophilic microalgal species onto ice sheet surfaces or into the troposphere to remove high volumes of $CO_2$ directly from the atmosphere and thereby to reduce or reverse the recent rise in global temperatures associated with human industrial activities. Like any inoculation, it is important that the species, dose, timing, and location are pre-determined for optimal planning and efficacy.

Post manufacture, versions of the Climate Vaccine may be deployed across a variety of environments, e.g., in the cloud layer of the troposphere and/or on existing natural ice sheets such as icebergs and ice sheets.

The troposphere is the lowest region of the atmosphere, extending from the earth's surface to a height of about 6-10 km (the lower boundary of the stratosphere). Photosynthesizing microorganisms within the clouds photosynthesize (convert $CO_2$ to biomass) utilizing sunlight energy to that fixes the $CO_2$ abundant in the troposphere into plant growth and replication. This process also releases valuable oxygen ($O_2$) back into the atmosphere. The equation for Photosynthesis $6CO_2+6H_2O \rightarrow C_6H_{12}O_6+6O_2$. $CO_2$ and water ($H_2O$) are abundant sources available in tropospheric clouds. These reactions are believed to occur at minuscule levels due to the negligible amounts of microorganisms naturally present in clouds. Embodiments of the present invention, by inoculating tropospheric clouds with the Climate Vaccine, increase this process by orders of magnitude.

The Tropospheric Algal Inoculation of Rubisco Climate Vaccine of the extremophile algae directly into clouds results in natural capture of $CO_2$ on a globally long-lasting, self-propagating widely distributed scale. The resulting algal blooms in the atmosphere are widely distributed across the globe by the ambient weather patterns and high level winds. The algal clumps resulting from practicing the invention act as natural condensation nuclei for precipitation to earth. Thus the invention can, in addition to its primary goal of sequestering atmospheric carbon, serve to also help calm extreme weather occurrences. Such deployment permits $CO_2$ capture rates on a megaton to gigaton scale.

BACKGROUND

Carbon dioxide ($CO_2$) is a greenhouse gas that is a major contributor to the increase in global temperature. It is proposed by the inventor that by administering psychrophilic microalgal species onto breakaway floating ice sheets and icebergs that the resulting cell growth on such surfaces will remove the high amounts of $CO_2$ directly from the atmosphere. This activity will reduce or even reverse the rise in global temperature to return closer to pre-industrial levels. Icebergs and are naturally occurring uninhabitable temporary floating structures which appear and disappear seasonally or cyclically. Floating ice sheets are distributed naturally by ocean currents and as such are ideal sites for utilizing the opportunity for carbon capture and deposition into the ocean biomass. The sea ice sheets are formed from fresh water rather than salt water, which is essential for the vaccine. It is proposed that by administering the vaccine onto breakaway floating ice sheets and icebergs that the resulting cell growth will remove the high levels of carbon dioxide directly from the atmosphere. This application permits $CO_2$ capture rates on a kiloton to megaton scale. The invention is also compatible for less motile, e.g., frozen lake surface, man made ice field or ice rink, snowcap, glacier, frozen canal or river, etc.

A main problem facing large scale carbon capture is the land requirement and the opportunity cost of re-purposing the land mass. Costs in terms of technology and energy are tremendous. This present invention fixes carbon from the atmosphere directly within the atmosphere utilizing low cost technology and low cost energy conversion avoiding the problematic re-purposing of land.

The Vaccine

Production of the Vaccine Itself Captures $CO_2$ on a Kiloton Scale

A first embodiment for manufacturing the Climate Vaccine features photobioreactors that are placed in industrial or other facilities that emit large amounts (higher than ambient concentrations) of $CO_2$. This embodiment in its simplest application converts industrial sourced $CO_2$ to solid biomass thus preventing atmospheric contamination. A second embodiment piggybacking on this, involves harvesting, packaging, and then deploying the biomass product in environments such as: ice rink units that are functionally constructed for direct capture of $CO_2$ from surrounding air, natural ice fields, including icebergs or ice sheets, atmospheric clouds, etc. The biomass invention is a product of Rubisco which has applied to it the name Climate Vaccine® aka: Rubisco Climate Vaccine®.

The RubisCO Climate Vaccine® (RCV) comprises a cultured cocktail of specifically optimized extremophile psychrophile micro-organisms, optimally together with a blend of constituent accelerants. The accelerants are selectable by the practitioner according to desired criteria, e.g., cost, volume, mass, mass:volume ratio, color, packaging, storage, regulation, etc. The cultured cocktail may comprise a single seed species or strain adapted to rapid growth and proliferation under culturing conditions approximating or mimicking conditions to be encountered in the select environment after local Vaccine deployment. For wider (non-specific) applications a cocktail not specific to a particular deployment zone may comprise two or more cultured species e.g., combined for distribution on the ice surface and/or in the atmosphere. The packaged plurality of species may be desired for general deployments when the optimal species or strain has not been addressed. The accelerants are optimally designed with the cultured cocktail for inoculation at specific locations to capture carbon dioxide directly from the atmosphere.

Post deployment, the vaccine is self-propagating as it consumes and removes $CO_2$ from its industrial or other facility or rink or ice field in the existing or natural environment. The Vaccine live elements absorb sunlight and $CO_2$ as they grow and proliferate forming progeny live elements that grow and proliferate. Pre-deployment, RSV can be readily stored in small 100 to 1,000 ml bottles or larger, jugs, barrels, tank, sized containers in ambient conditions, e.g., a ventilated warehouse, without any special requirements. Aqueous cultures may be further processed by lyophilization or freeze drying for compact long term storage and as an alternative to liquid prep-spraying at deployment. The reduced weight and volume of the lighter powdered format inoculant can result in lower cost deployment, larger inoculation area from a single inoculation run, increased dispersion, lessened logistical problems and a larger potential direct capture of gaseous $CO_2$ from the atmosphere.

In preferred embodiments, during RSV production, specifically site adapted portable Carbon Dioxide Removal (CDR) units at industrial sites that are producing significant $CO_2$ emissions to avoid atmospheric release of the site's $CO_2$. The CDR units are optionally further enabled by running commercially purchased photobioreactors in which regulated $CO_2$ will boost the growth and replication of the process. Commercially available units have remote sensing, analytical and data monitoring built in. They require minimum manual intervention, e.g., on a multi-day, weekly, bi-weekly basis. Commercial availability enables rapid uptake of this invention for general widespread use. Preferred units are the same size as the 20 ft shipping containers and therefore are easy to ship and deploy by common transport means and require minimal on-site set-up and very little space. Such units can be sited externally (outside an existing wall) or within a production facility that is producing $CO_2$. Flue gas or exhaust air is drawn into extraction units where carbon will be removed from the $CO_2$ intake into the bio-processor and resultant oxygen released into the atmosphere. Many industries produce large quantities of $CO_2$ during their processes including, but not limited to: steel, plastic, fertilizer manufacturers, brewers, bakers, yeast providers, and distilleries.

The food or distillation processes, e.g., for alcohol or breads, first involve fermentation by yeasts that consume carbohydrate food sources to form alcohol. A major byproduct from the metabolism is $CO_2$. A dedicated bioreactor fed with the fermentation emissions will capture the emitted $CO_2$ reducing the beverage's or bread's carbon footprint. But a secondary benefit arises from using the feed to grow the RC Vaccine These portable "$CO_2$ Removal Units" though reducing the carbon footprint of the associated plant, are thus primarily used to produce Rubisco Climate Vaccine® or analogous product. However, as previously mentioned, during vaccine production, they also operate as carbon removal facilities. This capture during the vaccine production phase, while significant, is on a smaller gross scale than achievable after vaccine deployment. Additionally, the units could be designed to produce by-products like, e.g., skin care and animal food additives during vaccine element propagation. CDR units can also operate under ambient conditions (capture atmospheric air). However higher levels of $CO_2$ are preferred to boost the CDR output performance, to possibly produce carbon credits, and to lower costs.

Relatively small amount, e.g., only about 100 ml of cells at 60,000 cells/ml, of the starter RCV vaccine is sufficient for deployment where the vaccine is transported to the deployment site(s) in a concentrated form. At the deployment site(s) the concentrated RCV is then diluted with water for wider spreading. Dilution rates are influenced by a number of factors, however the ratio is generally in the order of 8-10 parts per 1000, e.g., ˜8 ml per liter, therefore it is easy and economical to transport the vaccine for deployment for spraying or misting onto an extensive surface area. Freeze dried powder can serve as a RCV for aqueous suspension on-site or deployment as a sprayed powder.

Typical base cultures prior to dilution at dispersal site or for dilution prior to transport to the dispersal site may be maintained in a relatively concentrated stock, e.g., about 15,000 to 100,000 cells/ml. Cell numbers will depend on the practitioners plans, perhaps dependent on the route of dilution, size of cell, viscosity of medium, size of containers for culture and diluent, output of the CDR, etc. While typical dilutions are in the order of $10^2$, the precise dilution ratio is at the practitioners discretion. For example, a greater dilution may be used when higher volume/area ratios are required by the machinery. Final concentrations for easy delivery to the targeted zones may typically range from about 150,00 cells per liter or several fold higher cell concentrations, e.g., 500,000 to 750,000 cells per liter. Precise cell counts are not required for successful deployment. Ease of dilution and dispensing, volume or mass capacity of the delivery vehicle, fineness of the spray, available container sizes, etc., are several of the considerations a practitioner may consider in the stock and final concentrations. Thus a practitioner may at their discretion select a targeted concentration, e.g., about $1.75 \times 10^5$, $2 \times 10^5$, $3 \times 10^5$, $4 \times 10^5$, $4.5 \times 10^5$, $5 \times 10^5$, $6 \times 10^5$, $7 \times 10^5$, $8 \times 10^5$, $9 \times 10^5$, $10^6$, etc., dependent on equipment and factors at hand.

The locations for the dose, the amount and its developmental status for each inoculation is governed by threshold values and predicted levels of temperature, atmospheric pressure, humidity, diurnal light period and intensity that will enable optimized growth and replication efficacy until deposition in melt water or falling to the earth's surface. When desired, seed species may be harvested from the intended target or pre-deployed zone for additional serially culturing to form a vaccine with organisms biologically closer to those that thrived or were evolutionarily selected at the harvest zone and target site. Such intended site harvesting may increase acceptance by authorities of the public and also might serve to optimize (slightly improve) the survival longevity at the site and/or total carbon assimilated into biomass and removed from the atmosphere. For example, an organism naturally adapted to the dark-light cycles at a select latitude or location may, post serial adaptation for vaccine manufacture, improve carbon capture. Similar improvements may be seen in stock (off the shelf vaccines) where serial culturing incorporates a selected dark-light cycling.

The invention also applies to less-adapted or potentially un-adapted organisms. Such organisms when accompanied by growth accelerating nutrients, e.g., in suspension or solution with aqueous algae treatments and/or deployed as an additive at the algal deployment site; as component(s) in powder algal deployments result with enhanced carbon capture resulting from increased growth following deployment.

Serial culturing to produce vaccine ideally mimics the target conditions. For example, culture of some organisms is in bulk liquid, that may or may not be agitated, e.g., by bubbling or shaking. Propagation on sheet surfaces within the culture vessels is preferred as it more closely resembles the flat surface conditions or attachment to ice particles at the deployment zone. The organisms that are produced for the climate vaccine should be ideally be propagated and grown in conditions similar to what they will face post deployment. As an example, these organisms consume atmospheric $CO_2$ and thus are best allowed to grow and function at a liquid (surface of ice)-gas (atmosphere) interface. The extremophile psychrophile micro-organisms source organisms for vaccine adaptation optimally are propagated in conditions that let them form a film interface between liquid and gas. An organism coated membrane separating liquid feed from a $CO_2$ gas containing atmosphere is thus preferred.

Our most recent study indicates that a freeze dried algal culture formed as a fine powder, e.g., pellet average mass ~1-10×10$^{-4}$ g, permits simple deployment over a large area with significant gravitational draw for propulsion to its target proliferation site. Compared to aqueous suspension, the reduced payload weight and volume of the light powdered format inoculant onto floating sea ice or other surfaces will result in lower cost deployment, larger inoculation area, increased dispersion, lessened logistical problems and a larger potential direct capture of gaseous $CO_2$ from the atmosphere including troposphere, especially considering the logistics involved in deployment at extreme latitudes.

Optimistically, with general application of this invention on a global scale, initial conservative global modeling estimates by RubisCO Limited™ scientists calculated that with controlled deployment this invention has the capability of reducing $CO_2$ levels in the atmosphere to pre-industrial levels within a decade.

Secondary Effects

Oxygen—A By-Product of Assimilation of $CO_2$ During Photosynthesis Affects Earth's Climate Models of past eras show that oxygen ($O_2$) can influence global temperature and humidity as its concentration changes (Article in ANTHROPOCENE A Smithsonian magazine special report by Sarah Zelinski, Jun. 11, 2015).

Earth has a surprising new player in the climate game: $O_2$. Even though $O_2$ is not a heat-trapping greenhouse gas, its concentration in our atmosphere can affect how much sunlight reaches the ground, and new models suggest that that effect has altered climate in the past.

$O_2$ currently makes up about 21% of the gases in the planet's atmosphere, but that level hasn't been steady over Earth's history. For the first couple billion years, there was little $O_2$ in the atmosphere. Then, about 2.5 billion years ago, $O_2$ started getting added to the atmosphere by photosynthetic cyanobacteria. "Oxygen is produced as a waste product of photosynthesis. It is consumed through respiration," explains University of Michigan climate scientist Chris Poulsen, lead author of the study published in *Science*.

That $O_2$ waste product sparked a mass extinction known as the Great Oxygenation Event. But over time, new forms of life evolved that used or expelled $O_2$ in respiration, and atmospheric $O_2$ levels continued to increase. "The production and burial of plant matter over long periods causes $O_2$ levels to rise," explains Poulsen. Levels can fall again when that trapped ancient organic matter becomes exposed on land, and elements such as iron react with $O_2$ from the atmosphere, a reaction called oxidative weathering. As a result of these processes, atmospheric $O_2$ levels have varied from a low of 10% to a high of 35% over the last 540 million years or so.

Global Cooling by Releasing Oxygen

Poulsen and his colleagues were studying the climate and plants of the late Paleozoic, and during a meeting they started talking about whether $O_2$ levels might somehow have affected climate in the past. Studies have shown that atmospheric $CO_2$ has been the main climate driver through deep time, so most thought $O_2$'s role has been negligible.

But computer models based on carbon data have not been able to explain everything in the record. For example, the Cenomanian, an age in the late Cretaceous, was marked by high $CO_2$ and soaring temperatures, but models of this time usually spit out polar temperatures and precipitation rates that are too low when compared with data taken from the paleogeologic record. So Poulsen began modifying a climate model to test the $O2$ idea, and the results showed that changes in $O_2$ concentration did indeed have an impact through a series of feedbacks.

"Reducing oxygen levels thins the atmosphere, allowing more sunlight to reach Earth's surface," explains Poulsen. More sunlight lets more moisture evaporate from the planet's surface, which increases humidity. Because water vapor is a greenhouse gas, more heat gets trapped near Earth's surface, and temperatures rise. The increased humidity and temperature also leads to increases in precipitation. By contrast, when $O_2$ concentrations are higher, the atmosphere gets thicker and scatters more sunlight. As a result, there is less water vapor to trap heat.

Whereas rainforests get most of the popular credit for $O_2$ production, microscopic algae produce at least 50% of the Earth's $O_2$. Most conventional methods of Direct Air Capture involve sequestering $CO_2$, e.g., within minerals, etc., which serve to remove and long term sequestrate both the carbon and its originating combined life giving $O_2$ from the atmosphere.

Carbon dioxide ($CO_2$) is identified as a greenhouse gas that is a major contributor to the increase in global temperature. Removing high levels of the heat absorbing carbon dioxide from the atmosphere can reduce the rise in global temperature. The present invention provides product and methods that can ingest carbon dioxide from air flowing by, over, or around the product, hereinafter vaccine, or RubisCO Climate Vaccine®, sequester carbon within product elements, produce (self-propagate) additional functional vaccine elements, precipitate to ground or water. Following precipitation, the vaccine, including progeny elements, integrates into the algal pathways, providing a link in the food chain and more permanent deposition of the sequestered carbon as detritus/muck.

The vaccine comprises a live microorganism that post deployment converts gaseous $CO_2$ to a solid carbon deposit that can sequester the carbon for days as perhaps 20% enters the food chain with the remaining 80% being sequestered essentially permanently.

Whilst it is known that many microorganisms utilize carbon dioxide from the atmosphere to photosynthesize, the invention is unique in that it is a specifically designed and cultured cocktail of constituent ingredients and developmental stages of the microorganisms to enable optimized growth in the extreme atmospheric conditions for its deployed inoculation. The location for the dose, the amount, its developmental status for each inoculation is governed by threshold values of temperature, atmospheric pressure, humidity, diurnal light period and intensity and predicted patterns of environmental distribution that will enable optimized growth and replication efficacy over the period from its initial inoculation until its deposition. Whilst its growth and replication is a naturally occurring process the vaccine is inoculated into new and previously microorganism un-colonized environments.

The preferred Climate Vaccine is a cocktail of selected cultured extremophile psychrophile microorganisms specific for enhanced or optimal growth and hence carbon capture in the ambient culture conditions. Ambient culture conditions are selected to approximate or to mimic cold conditions where the microorganisms are to be deployed. The Climate Vaccine algal elements are cultured to a specific concentration density for packing and deployment at the intended target. Prior to deployment, the cultured population is combined with minerals added in liquid or solid form with a tendency to optimize growth, and hence, carbon capture in the target ambient conditions, such as solid icy surface, a cloud zone, a cold culture device, etc. The Climate Vaccine contains the live elements in a relatively quiescent state in mixture with inorganic trace nutrients that serve as growth accelerants. A preferred Climate Vaccine contains inert light absorbing particles as accelerant growth nuclei. The resultant Climate Vaccine can be transported and stored in diluted or concentrated liquid form for long periods in cool, light proof containers. The Climate Vaccine origin cultured phials/agar slopes should ideally be refrigerated at a temperature below 4° C. These storage conditions will minimize potential biomass degradation or adaptive counter culturing during mid- to long-term storage. Climate Vaccine may be packaged as a solid desiccated powder for later suspension in a liquid carrier (for aqueous deployment as a finely dispersed mist) or for spraying as powder into or onto the deployment zone.

As the cultured cocktail "grows" each living element becomes larger and divides producing progeny elements. These progeny continue to consume ambient $CO_2$ and to grow and proliferate exponentially compounding offspring.

During the production phase, the Climate Vaccine is cultured to a desired concentration density for packaging and distribution at the intended target site. In preferred embodiments, for atmospheric deployment, in addition to the cultured psychrophile microorganisms: the Climate Vaccine comprises inorganic nutrients as growth accelerants with inert light absorbing particles as accelerant growth nuclei. During culture growth accelerants may be fed to the culture continuously or at timed stages to correspond to other conditions such as light cycle, fermentation cycle, industrial process, etc.

After the preparation growth stage, the Climate Vaccine can be transported and can be stored in a diluted or as a concentrated form for long periods in cool light proof containers. Absent light, the cultures maintain dormancy, but are activated when dispersed and exposed to light. Optimally, the Climate Vaccine is refrigerated at a temperature below 4° C. to minimize potential biomass degradation in mid to long term storage. Freeze drying may be applied for easier transport to the deployment site and a lighter payload for dispersal.

The cultured cocktail for atmospheric or industrial $CO_2$ removal is dispensed as a bio-sustainable microalgae cocktail to capture carbon dioxide directly from its ambient gas. The cocktail may be in a liquid or solid form. Inorganic accelerants in the Climate Vaccine increase the absorption of light wavelengths corresponding to the chlorophyll(s) and also less specifically converting light energy to heat thereby heating the micro-environment of each algal entity. Accelerants can provide nutrient and light absorbent components to accelerate algal growth. A simple low cost accelerant may comprise soil or other light absorbing material obtained prior to culture, during culture or at the deployment site to absorb solar energy and locally increase the temperature to stimulate the algal growth at the deployment site.

The preferred carrier medium enables sustainable deployment providing a dispersible suspension of viable algal concentrate. Accelerants and feed nutrients may be included in the vaccine to optimize growth/reproduction.

Vaccine Development

Snow or glacial algae are found on all continents, and most species are in the Chlamydomonadales (Chlorophyta) and Zygnematales (Streptophyta). Other algal groups include euglenoids, cryptomonads, chrysophytes, dinoflagellates, and cyanobacteria. They can live under extreme conditions of temperatures near 0° C., high irradiance levels in open exposures, low irradiance levels under tree canopies or deep in snow, acidic pH, low conductivity, and desiccation after snow melt. These primary producers may color snow green, golden-brown, red, pink, orange, or purple-grey, and they are part of communities that include other eukaryotes, bacteria, archaea, viruses, and fungi. They are an important component of the global biosphere and carbon and water cycles. Life cycles in the *Chlamydomonas-Chloromonas-Chlainomonas* complex include migration of flagellates in liquid water and formation of resistant cysts. Selected strains of these algae have potential for producing food or fuel products. Organisms regarded as true snow and glacial algae thrive in a liquid water film between melting snow and ice crystals, and usually do not propagate outside of this habitat. Serial culturing to formulate the vaccine should select for growth at liquid-gas interface.

Snow and glacial algae are examples of how life can adapt to harsh environmental conditions in terms of solar irradiance, low temperatures or nutrients, and show that phototroph extremophiles perform well in putative extreme habitats such as melting snowpacks or glacial surfaces. As a result, these microbes have been considered as Earth analogs for life outside our planet (Havig and Hamilton 2019, Vimercati et al. 2019b). When there is liquid water, the algae can reproduce and bloom within days or weeks. During this time, they can start green, then turn red, or stay green or stay red—it depends on the algal species. Such microorganisms have adapted (evolved) to survive under a wide variety of conditions. As all living organisms, when they grow, they metabolize nutrients to form their biomolecular structures. For photosynthetic organisms an important nutrient is $CO_2$.

Glacier algae photosynthesize at surprisingly high rates considering their thermodynamically unfavorable cold environment (Remias et al., 2009, 2012a; Cook et al., 2012; Yallop et al., 2012; Williamson et al., 2018). Recent estimates of glacier algal net productivity in southwestern Greenland ranged from ~0.5 to 1 mg C $l^{-1}$ $d^{-1}$, based on ice containing dense algal communities (~104 cells $ml^{-1}$; Yallop et al., 2012; Williamson et al., 2018). While few attempts have been made to constrain the importance of glacier algae for supraglacial carbon budgets, recent modeling efforts for regions of the southwestern GrIS have highlighted the major contribution that blooms can make to supraglacial carbon fixation (Cook et al., 2012; Williamson et al., 2018), with an average net carbon fixation of ~16±8 kg C $km^2$ estimated for the 2016 ablation season (Williamson et al., 2018). This can lead to accumulation of autochthonous organic carbon within glacier algal-rich habitats (Musilova et al., 2017). Labile organic carbon not consumed in situ by secondary production may be exported via meltwater flushing for utilization within downstream subglacial and periglacial ecosystems (Musilova et al., 2017; Smith et al, 2017).

Blooms of algae on glacier and ice sheet surfaces have been reported from across the cryosphere, including Antarctica (Ling and Seppelt, 1993), Alaska (Takeuchi, 2001, 2013; Ganey et al, 2017), Siberia (Takeuchi et al, 2006, 2015; Tanaka et al, 2016), the Himalayas (Yoshimura et al, 1997), Svalbard (Remias et al, 2012a), and Greenland (Uetake et al, 2010; Yallop et al, 2012; Stibal et al, 2017; Williamson et al, 2018), indicating their apparent ubiquity in supraglacial systems. Blooms initiate following snow line retreat, with algal biomass observed to increase in surface ice through time (Stibal et al, 2017; Williamson et al, 2018). In contrast to snow algae (Hoham and Duval, 2001), the absence of a flagellated life stage prevents active motility of glacier algae, and thus, colonization of new ice environments during bloom events is likely dependent on local hydrological or aeolian forcing (Kristiansen, 1996). On the Greenland Ice Sheet (GrIS), population doubling times have been estimated at 3.75-5.5 days (Stibal et al, 2017; Williamson et al, 2018), with cell densities observed to range from 9.1×104 to 29.5×104 cells ml-1 at marginal locations (Yallop et al, 2012), from <100 to $8.5 \times 10^4$ cells ml$^{-1}$~30 km into the south-westerly region of the ice sheet (Stibal et al, 2017), and from 1.6×104 cells ml-1 to 0 cells ml-1 from ~30 km inland to the snow line (Williamson et al, 2018). The influences on spatial patterning in biomass are multifaceted. Observations of algal biomass on mountain glaciers (e.g, Yoshimura et al 1997; Takeuchi and Kohshima, 2004; Takeuchi et al, 2009) show declines in biomass with increasing altitude, while observations from the GrIS's "dark zone" (a conspicuous area of dark ice that appears across the west and southwestern sectors of the ice sheet each summer; Wientjes and Oerlemans, 2010) show a decrease in biomass away from the ice sheet margin (Williamson et al, 2018). Considered jointly, these intimate that longer melt seasons support algal biomass development through promoting solar radiation input, nutrient availability, and diminished snow cover (Yoshimura et al, 1997). Decreases in biomass can be driven by rainfall-associated flushing events (Stibal et al, 2017), and biomass is potentially restricted close to the terminus of glaciers by mineral dust covering that can limit photosynthesis and/or by increased meltwater flushing on steeper slopes (Takeuchi, 2013). Interspeccial interactions also influence the relative dominance of glacier algae at the glacier scale, with specialists dominating more stable ice environments and generalist species becoming dominant in areas characterized by less stable conditions, e.g., frequent changing between snow and ice environments (Yoshimura et al, 1997).

It has been shown in situ in that snow algae have the capability of capture of 257 tonnes of carbon Km$^{-2}$ year$^{-1}$ (Andrew Gray, et al, 2021).

The naturally occurring wild type of the microorganism species used as source material for the vaccine, flourish and capture carbon dioxide in large amounts where they grow. This invention culturally modifies wild type organisms for optimal activity at the target site where Climate Vaccine is administered as a growth optimized cocktail directly at the site in quantities for accelerated carbon capture.

The Climate Vaccine is superior to other Carbon Capture alternatives, yet is proposed for use in conjunction with many similarly purposed activities.

A visually striking adaptation of glacier algae to their environment is the production of a specialist pigment absorbing ultraviolet and visible light (purpurogallin carboxylic acid-6-O-Beta-D-glucopyranoside), contained within lipid bodies and vacuoles occupying a large proportion of the cell; Remias et al, 2009, 2012a, b). In addition to the suite of light-harvesting and photoprotective pigments typical of green microalgae (Remias et al, 2009, 2012b; Williamson et al, 2018), this phenolic pigment is primarily assumed to serve a photoprotective role, shading the underlying chloroplasts from the significant PAR and UV regime apparent in supraglacial systems (Remias et al, 2009, 2012b; Williamson et al, 2018). It also likely serves to convert the abundant light energy to heat, allowing melt water generation local to the cell (Dial et al, 2018). To date, the capacity of glacier algal phenols to provide photoprotection has been indirectly evidenced by a lack of saturation during photosynthesis-irradiance curves (Remias et al, 2012a, b) and fluorescence-based rapid light curves (Yallop et al, 2012), ranging up to 2000 μmol photons m$^2$/s. Given that the photosynthetic machinery is adversely affected by several cold associated stressors (i.e., freezing and desiccation reduce cell membrane fluidity impacting electron transport; low temperatures mimic high-light stress by decreasing the efficiency of metabolic electron sinks; Lyon and Mock, 2014), it is likely that glacier algae purpurogallins serve to protect the cell against multiple stressors. Little further information on specific glacier algae adaptations to life in surface ice is available, with this knowledge gap strongly exacerbated by their reluctance to be cultured under laboratory conditions (Remias el al, 2009, 2012a). Though conjugation in *A. nordenskioldii* field populations has been observed in Svalbard (Remias el al, 2012a, b) and the GrIS (C. Williamson, personal observation), the production of a dormant zygospore does not appear to be an overwintering strategy, with glacier algae observed to overwinter in a non-cyst-like, vegetative state (Remias et al, 2009). This likely permits rapid resumption of physiological activity on initiation of the relatively short summer growth season. Glacier algae also demonstrate increased concentrations of sugars and polyols (i.e., compatible solutes) (Roser el al, 1992; Chapman el al, 1994), consistent with known cold tolerance mechanisms in other psychrophilic microalgae (Welsh, 2006; Casanueva et al, 2010; Lyon and Mock, 2014). However, knowledge on other features typically associated with cold tolerance in microalgae, e.g., membrane fluidity, production of specialist enzymes, "coldshock" proteins or extracellular polymeric substances, is currently lacking.

Blooms of algae are known to occur in snow when air temperatures can remain at or above freezing for extended periods of time. However, hard freezes may occur after snow algae make their appearance, and some species survive this environmental stress more easily than others. Three species of snow algae, *Raphidonema nivale*, *Chloromonas pichinchae*, and *Cylindrocystis brébissonii*, were isolated into axenic culture for optimum temperature studies under set laboratory conditions. In those temperatures tested (1, 5, 10, 15, and 20° C.), it was found that optimum growth for *R. nivale* occurred at 5° C., for *C. pichinchae* at 1° C., and for *C. brébissonii* at 10° C. Three other species of snow algae, *Chlainomonas kolii, Chlainomonas rubra*, and *Chlamydomonas nivalis* (from Washington snow), did not grow in defined medium for extended periods of time. Vegetative cells of *C. kolii* and *C. rubra* lose their flagella at temperatures above 4° C. as observed on a cooling stage, and optimum growth for these species probably occurs at a temperature below 5° C. *C. nivalis* resting spores cleave into daughter cells at temperatures from 0 to 20° C., and perhaps this observation may be used as an indicator for optimum growth in this species. (Ronald W. Rohan 24 May 2018).

Species of snow algae used in this study and in previous studies are compared with respect to their optimum temperature and temperature range for growth. Species that do not grow at temperatures above 10° C. and have optimum growth at lower temperatures are classified here as true snow algae. This list of species includes *Chlainomonas kolii, Chlainomonas rubra, Chlamydomonas nivalis* (cultures of Hoham from Washington snow), *Chloromonas pichinchae, Chloromonas* sp., *Raphidonema tatrae, Chromulina chionophila* (cultures of Stein), and *Cryptomonas frigoris* (Heymsfield et al).

Rain bearing Precipitating Winter Clouds have a top brightness temperature 0-5° C. defining the specific range of snow algal species suitable for cloud inoculation.

The Climate Vaccine works faster than any known nature based alternatives. In natural occurring conditions it has been shown to assimilate 65% of irradiated $^{14}C$ carbon dioxide in just three hour. It exceeds known alternatives for capturing large scale amounts of carbon dioxide directly from the atmosphere. Active constituent organisms of the vaccine have been measured as capturing 40 times more carbon than an Amazonian rain forest per square meter. The growing algae in active culture can withstand high levels of UV radiation (sunlight) as well as intense daily changes in temperature (−20° C. to +35° C.) including common storage and transport temperatures (−20° C. to +20° C.). Freeze dried product can withstand even greater temperature extremes. Whilst experiments continue to prove long-time durability, current observations of the cultured freeze-dried powder are showing survival of the freeze-dry process as indicated by color changes of green to red a marker to show that growth has and is occurring in all our samples.

The aqueous vaccine can be transported and stored at ambient (non-refrigerated temperatures). The long-term (multi-month) survivability of these extremophile algae as well other tested unicellular organisms has been demonstrated under exposure to wide temperature variations, UV radiation, and desiccation as encountered in space. See, e.g., Can organisms survive on Mars, and can we identify them?. Mar. 26, 2019|Results of the BIOMEX experiment. DLR Institute of Planetary Research. Astrobiology BIOMEX issue, 2019 February (Vol. 19, Issue 2, 2019).

The cultured organisms can withstand low and high levels of humidity and atmospheric pressure, including water immersion in a concentrated vaccine supply. The vaccine elements are photosynthetically active at temperatures up to at least 27° C., temperatures much higher than found in clouds or on ice. $CO_2$ assimilation rates are seen to increase with increasing levels of $CO_2$ up to at least 12 ppm levels. This far exceeds current $CO_2$ in the environment (4 ppm) so even if $CO_2$ levels massively rise, the Climate Vaccine will remain effective. During production, e.g., as the vaccine consumes and sequesters carbon from the $CO_2$ it returns free gaseous oxygen ($O_2$) to the atmosphere from previously combined oxygen in $CO_2$ rather than alternative sequestration methods, such as carbonate depositing. The environmental vaccination is more efficient and less intrusive than other recognized nature based solutions for climate change, e.g., re-forestation.

EXAMPLES

Specific species of psychrophile algae were initially chosen for the initial vaccine trial product. Samples of wild type Antarctic snow algae: *Chlamydomonas nivalis* (CN) and *Chloromonas pichinchae* (CP) were purchased from UTEX in Texas, US. Proof of durability was seen when the purchased products were impounded by authorities for over ten days. Viability of the cultures was maintained even after the low pressures and temperatures in the plane cargo hold and normal storage conditions during the impoundment period.

The algae were serially cultured in 3N-BBM+V medium from a 1000 ml CCAP prepared from stock solutions:

| | |
|---|---|
| NaNO$_3$ | 25.0 g |
| CaCl$_2$•2H$_2$O | 2.5 g |
| MgSO$_4$•7H$_2$O | 7.5 g |
| K$_2$HPO$_4$•3H$_2$O | 7.5 g |
| KH$_2$PO4 | 17.5 g |
| NaCl | 2.5 g | with trace elements prepared in a stock of 0.75 g EDTA in 1000 ml distilled water added in the exact following sequence:

| | |
|---|---|
| FeCl$_3$•6H$_2$O | 97.0 mg |
| MnCl$_2$•4H$_2$O | 41.0 mg |
| ZnCl$_2$ | 5.0 mg |
| CoCl$_2$•6H$_2$O | 2.0 mg |
| Na$_2$MoO$_4$•2H$_2$O | 4.0 mg | and two vitamin supplements:

| | |
|---|---|
| Thiaminhydrochloride (B1) | 120 mg in 100 ml distilled water-sterile filtered |
| Cyanocobalamin (B$_{12}$) | 100 mg in 100 ml distilled water then diluted: 1 ml into 99 ml distilled water-sterile filtered |

From these stocks, the 3N-BBM+V medium is made by combining:

| | |
|---|---|
| NaNO$_3$ | 30.0 ml |
| CaCl$_2$•2H$_2$O | 10.0 ml |
| MgSO$_4$•7H$_2$O | 10.0 ml |
| K$_2$HPO$_4$•3H$_2$O | 10.0 ml |
| KH$_2$PO$_4$ | 10.0 ml |
| NaCl | 10.0 ml |
| trace elements | 6.0 ml |
| B$_1$ | 1.0 ml |
| B$_{12}$ | 1.0 ml |

CN and CP samples were then cultured on agar slopes and phial solutions to obtain desired quantities and concentrations 60,000 to $10^6$ cells/ml for viability testing.

While the inventor used the term "we" or "our" in describing this invention, it is to be understood that the inventor conceived the claimed inventions. The inventor directed associates in developing and practicing the processes described herein. Associates also confirmed as "second eyes" reported observations.

The invention claimed is:

1. A carbon sequestration vaccine comprising:
   a) a cultured cocktail of extremophile psychrophile microalgae selected for enhanced growth and proliferation in extreme cold conditions; and
   b) feed and mineral accelerants, wherein (a) and (b) are in the form of dry powder granules.

2. The carbon sequestration vaccine of claim 1 wherein said cocktail comprises a plurality of microalgae species.

3. The carbon sequestration vaccine of claim 1 wherein said extremophile psychrophile micro-organisms are selected from at least one genus selected from the group consisting of: Chlamydomonadales (Chlorophyta), and Zygnematales (Streptophyta).

4. The carbon sequestration vaccine of claim 1 wherein said extremophile psychrophile micro-organisms are selected from at least one species selected from the group consisting of: *Chlainomonas kolii, Chlainomonas rubra, Chlamydomonas nivalis, Chloromonas pichinchae, Chloromonas* sp., *Raphidonema tatrae, Chromulina chionophila,* and *Cryptomonas frigoris.*

5. The carbon sequestration vaccine of claim 1, wherein said extreme cold conditions comprise the temperature of an ice surface.

6. The carbon-sequestration vaccine of claim 5 wherein said extremophile psychrophile microalgae is adapted for enhanced growth and proliferation on said ice surface in a dry granular form.

\* \* \* \* \*